United States Patent [19]

Chiang

[11] Patent Number: 6,046,361
[45] Date of Patent: Apr. 4, 2000

[54] POLYORGANOFULLERENES

[76] Inventor: Long Y. Chiang, 4F, #15, Lane 97, Shin-Sheng S. Road, Sec. 1, Taipei, Taiwan

[21] Appl. No.: 08/976,532

[22] Filed: Nov. 20, 1997

Related U.S. Application Data

[63] Continuation-in-part of application No. 08/893,055, Jul. 15, 1997, which is a continuation-in-part of application No. 08/547,714, Oct. 26, 1995, Pat. No. 5,648,523.

[51] Int. Cl.[7] .................................................. C07C 304/01
[52] U.S. Cl. ........................................... 564/458; 568/817
[58] Field of Search .............................. 564/458; 568/817

[56] References Cited

U.S. PATENT DOCUMENTS

| | | | |
|---|---|---|---|
| 5,177,248 | 1/1993 | Chiang et al. | 560/86 |
| 5,294,732 | 3/1994 | Chiang et al. | 560/86 |
| 5,416,188 | 5/1995 | Chiang et al. | 528/291 |

FOREIGN PATENT DOCUMENTS

| | | |
|---|---|---|
| 0 653 424 A1 | 5/1995 | European Pat. Off. . |
| WO 95/19949 | 7/1995 | WIPO . |

OTHER PUBLICATIONS

Belik et al., "Reaction of Buckminsterfullerene with orth–Quinodimethane: a New Access to Stable $C_{60}$ Derivatives", Angew. Chem. Int. Ed. Engl. 1:78–80, 1993.

Chiang et al., "Efficient Synthesis of Polyhydroxylated Fullerene Derivatives via Hydrolysis of Polycyclosulfated Precursors", J. Org. Chem., 59:3960–3968, 1994.

Chiang et al., "Evidence of Hemiketals Incorporated in the Structure of Fullerols Derived from Aqueous Acid Chemistry", J. Am. Chem. Soc., 115:5453–5457, 1993.

Chiang et al., "Free Radical Scavenging Activity of Water–soluble Fullernols", J. Chem. Soc. Chem. Commun., 1283–1284, 1995.

Chiang et al., "Multi–hydroxy Additions onto $C_{60}$ Fullerence Molecules", J. Chem. Soc. Chem. Commun., 1791–1793, 1992.

Chiang et al., "Versatile Nitronium Chemistry for $C_{60}$ Fullerene Functionalization", J. Am. Chem. Soc., 114:10154–10157, 1992.

Friedman et al., "Inhibition of the HIV–1 Protease by Fullerence Derivatives: Model Building Studies and Experimental Verification", J. Am. Chem. Soc, 115:6506–6509, 1993.

Hirsch et al., "Globe–trotting Hydrogens on the Surface of the Fullerence Compound $C_{60}H_6(N(CH_2CH_2)_2O)_6$", Angew. Chem. Int. Ed. Engl. 30:1309–1310, 1991.

Hoke et al., "Reaction of Fullerenes and Benzyne", J. Org. Chem. 57:5069–5071, 1992.

Isaacs et al., "Improved Purification of $C_{60}$ and Formation of γ and II–Homoaromatic Methano–Bridged Fullerenes by Reaction with Alkyl Diazoacetates", Helvetica Chimica Acta 76:1231–1250, 1993.

Juha et al., "Reactivity of Fullerenes with Chemically Generated Singlet Oxygen", J. Chem. Soc., Chem. Commun., 2437–2438, 1994.

Krusic et al., "Radical Reactions of $C_{60}$", Science 254:1183–1185, 1991.

Li et al., "$C_{60}$ Fullerol Formation Catalysed by Quaternary Ammonium Hydroxides", J. Chem. Soc., Chem. Commun. 1784–1785, 1993.

Paulus et al., "Diethyl Methano–$C_{60}$–fullerene–61,61–dicarboxylate Chloroform Solvate at 193K, $C_{60}C(CO_2C_2H_5)_2$ $CHCl_3$", Acta Cryst, C51:143–146, 1995.

Prato et al., "[3+2] and [4+2] Cycloadditions of $C_{60}$", J. Am. Chem. Soc. 115:1594–1595, 1993.

Shu et al., "Reaction of [80]Fullerene with 1–(4–Methoxyphenyl)–1–(trimethylsilyloxy)ethylene", J. Chem. Commun. 367–368, 1995.

Roy et al., "$NO_2$ Adducts of $C_{60}$: Synthesis of Polynitro–Polyhydroxy Fullerenes", J. Chem. Soc., Chem. Commun. 275–276, 1994.

Balch et al., "Supramolecular Aggregation of an $(90^{2-}-C_{60})$ Iridium Complex Involving Phenyl Chelation of the Fullerene", J. Am. Chem. Soc. 114:5455–5457, 1992.

Suzuki et al., "Systematic Inflation of Buckminsterfullerene $C_{60}$: Synthesis of Diphenyl Fulleriods $C_{61}$ to $C_{66}$", Science 254:1186–1188, 1991.

Taliani et al., "Light–induced Oxygen Incision of $C_{60}$", J. Chem. Soc. Chem. Commun., 220–222, 1993.

Tokuyama et al. "Photoinduced Biochemical Activity of Fullerene Carboxylic Acid", J. Am. Chem. Soc. 115:7918–7919, 1993.

Tsuda et al, "Addition Reaction of Benzyne to $C_{60}$", Chemistry Letters 2333–2334, 1992.

Wilson et al., "A New Reaction of Fullerenes: [2+2] Photocycloaddition of Enones", J. Am. Chem. Soc. 115:8495–8496, 1993.

Balch et al., "Supramolecular Aggregation of an $(529^{2-}-C_{60})$ Iridium Complex Involving Phenyl Chelation of the Fullerene", J. Am. Chem. Soc. 114:5455–5457, 1992.

Chiang et al., "Pharmacology", Chemical Abstracts vol. 122, No. 23, Jun. 5, 1995, Abstract No. 281924.

Chiang et al., "Pharmacology", Chemical Abstracts vol. 124, No. 9, Feb. 26, 1996, Abstract No. 106531.

Chiang, et al., "Free–Radical Scavenging Effect of Water–Soluble [60] Fullerenols in Whole Blood . . . ", Proc.Electrochem.Soc. 95–10, 699 (1995).

Huang, et al., "Antiproliferative Effect of Polyhydroxylated $C_{60}$ on Vascular Smooth Muscle Cells", Proc.Electrochem.Soc. 96–10, 403 (1996).

*Primary Examiner*—Robert Gerstl
*Attorney, Agent, or Firm*—Fish & Richardson P.C.

[57] ABSTRACT

Polyorganofullerene and polyhydroxyorganofullerene derivatives have the respective formulas, F—$(E)_n$ and F—$(E)_n$—$(OH)_m$, in which F is a fullerene core; E is a nucleophilic substituent; —OH is a hydroxy group; n is 2–30; and m is 1–20. Also disclosed is a method of preparing such polyorgano-fullerene and polyhydroxyorganofullerene derivatives using polynitrofullerenes or polycyclosulfated fullerenes as intermediates.

18 Claims, No Drawings

POLYORGANOFULLERENES

CROSS REFERENCE TO RELATED APPLICATIONS

This application is a continuation-in-part of U.S. Ser. No. 08/893,055, filed Jul. 15, 1997, which, in turn, is a continuation-in-part of U.S. Ser. No. 08/547,714, filed Oct. 26, 1995, now U.S. Pat. No. 5,648,523.

BACKGROUND OF THE INVENTION

Since the discovery of fullerenes, a number of their poly-substituted derivatives have been reported. For example, polyalkylfullerene derivatives can be prepared by reacting fullerenes with organic alkyl lithium or alkyl Grignard reagents and then with alkyl halides [Wudl, et al., ACS Symp. Ser. 1992, 481, 161], or directly with organic radicals [Krusic, et al., Science 1991, 254, 1183]. On the other hand, enones react with fullerenes to afford polycycloalkylfullerene derivatives [Wilson, et al., J. Am. Chem. Soc. 1993, 115, 8495]. As another example, polyalkylaminofullerene derivatives is synthesized by reacting fullerenes with alkyl amine [Hirsch, et al., Angew. Chem. Int. Ed. Engl. 1991, 30, 1309]. Some of the above-mentioned reactions, however, suffer from low yields and long reaction time.

SUMMARY OF THE INVENTION

An aspect of this invention relates to a polyorganofullerene derivative of the following formula:

$$F(\text{---E})_n$$

wherein F is a fullerene core;
each E, independently, is $E_1$, $E_2$, $E_3$, $E_4$, or $E_5$,
in which
 each $E_1$, independently, is $Y_1,Y_2$-amino, $(Y_1,Y_2\text{-alkyl})$-amino, $Y_1,Y_2$-ethylenediamino, (dihydroxymethyl)alkylamino, $(X_1,X_3$-aryl)amino, or $X_1,X_3$-aryloxy; each $E_2$, independently, is $Y_1,Y_2$-alkoxy, $(Y_1,Y_2$-amino)alkoxy, $(Y_1,Y_2,Y_3$-aryl)oxy, (dihydroxyalkyl)aryloxy, $(Y_1,Y_2,Y_3$-alkyl)amino, $(Y_1Y_2,Y_3$-aryl)amino, or dihydroxyalkylamino; each $E_3$, independently, is $Y_1,Y_2,Y_3$-alkoxy, (trihydroxyalkyl)alkoxy, (trihydroxyalkyl)alkylamino, (dicarboxyalkyl)amino, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl; each $E_4$, independently, is ((glycosidyl)oxoheteroaryl)amino, ((glycosidyl)oxoaryl)amino, $(X_1,X_2,X_3$-heteroaryl)amino, $(X_1$-diarylketone)amino, $(X,X_1$-oxoaryl)amino, $(X,X_1$-dioxoaryl)amino, $(Y_1$-alkyl,$Y_2$-alkyldioxoheteroaryl)amino, $(Y_1$-alkyl,$Y_2$-alkyldioxoaryl)amino, (di$(Y_1,Y_2$-methyl)dioxoheteroaryl)amino, (di$(Y_1,Y_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl)amino, ((isopropylaminohydroxy-alkoxy)aryl)amino, or $(X_1,X_2,X_3$-alkylaryl)amino; each $E_5$, independently, is $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(X,X_1$-oxoaryl)oxy, $(X_1,X_2$-dioxoaryl)oxy, $(Y_1,Y_2$,diaminodihydroxy) alkyl, $(X_1,X_2$-heteroaryl)thio, ((tricarboxylalkyl)ethylenediamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$,-alkyl(thiocarbonyl)thio, $Y_1,Y_2,Y_3$-alkyl(thiocarbonyl)thio, $(Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-20}$amino, or (pyranosyl) amino; each X, independently, is halide; each of $X_1$ and $X_2$, independently, is —H, —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; each $X_3$, independently, is —$Y_1$, —O—$Y_1$, —S—$Y_1$, —NH—$Y_1$, —C—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; each of $Y_1$, $Y_2$, and $Y_3$ independently, is —B—Z; each B, independently, is —$R_a$—O—[Si(CH$_3$)$_2$—O—]$_{1-100}$, $C_{1-2000}$ alkyl, $C_{6-40}$ aryl, $C_{7-60}$ alkylaryl, $C_{7-60}$ arylalkyl, $(C_{1-30}$ alkyl ether)$_{1-100}$, $(C_{6-40}$ aryl ether)$_{1-100}$, $(C_{7-60}$ alkylaryl ether)$_{1-100}$, $(C_{7-60}$ arylalkyl ether)$_{1-100}$, $(C_{1-30}$ alkyl thioether)$_{1-100}$, $(C_{6-40}$ aryl thioether)$_{1-100}$, $(C_{7-60}$ alkylaryl thioether)$_{1-100}$, $(C_{7-60}$ arylalkyl thioether)$_{1-100}$, $(C_{2-50}$ alkyl ester)$_{1-100}$, $(C_{7-60}$ aryl ester)$_{1-100}$, $(C_{8-70}$ alkylaryl ester)$_{1-100}$, $(C_{8-70}$ arylalkyl ester)$_{1-100}$, —R—CO—O—$(C_{1-30}$ alkyl ether)$_{1-100}$, —R—CO—O—$(C_{6-40}$ aryl ether)$_{1-100}$, —R—CO—O—$(C_{7-60}$ alkylaryl ether)$_{1-100}$, —R—CO—O—$(C_{7-60}$ arylalkyl ether)$_{1-100}$, $(C_{4-50}$ alkyl urethane)$_{1-100}$, $(C_{14-60}$ aryl urethane)$_{1-100}$, $(C_{10-80}$ alkylaryl urethane)$_{1-100}$, $(C_{10-80}$ arylalkyl urethane)$_{1-100}$, $(C_{5-50}$ alkyl urea)$_{1-100}$, $(C_{14-60}$ aryl urea)$_{1-100}$, $(C_{10-80}$ alkylaryl urea)$_{1-100}$, $(C_{10-80}$ arylalkyl urea)$_{1-100}$, $(C_{2-50}$ alkyl amide)$_{1-100}$, $(C_{7-60}$ aryl amide)$_{1-100}$, $(C_{8-70}$ alkylaryl amide)$_{1-100}$, $(C_{8-70}$ arylalkyl amide)$_{1-100}$, $(C_{3-30}$ alkyl anhydride)$_{1-100}$, $(C_{8-50}$ aryl anhydride)$_{1-100}$, $(C_{9-60}$ alkylaryl anhydride)$_{1-100}$, $(C_{9-60}$ arylalkyl anhydride)$_{1-100}$, $(C_{2-30}$ alkyl carbonate)$_{1-100}$, $(C_{7-50}$ aryl carbonate)$_{1-100}$, $(C_{8-60}$ alkylaryl carbonate)$_{1-100}$, $(C_{8-60}$ arylalkyl carbonate)$_{1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—$(C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester)$_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—$(C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—$(C_{2-50}$ alkyl amide, $C_{7-60}$ aryl amide, $C_{8-70}$ alkylaryl amide, or $C_{8-70}$ arylalkyl amide)$_{1-100}$; each Z, independently, is —C—D—, wherein C, independently, is —R—, —R—Ar—, —Ar—R—, or —Ar—; and D, independently, is —OH, —SH, —NH$_2$, —NHOH, —SO$_3$H, —OSO$_3$H, —COOH, —CONH$_2$, —CO—NH—NH$_2$, —CH(NH$_2$)—COOH, —P(OH)$_3$, —PO(OH)$_2$, —O—PO(OH)$_2$, —O—PO(OH)—O—PO (OH)$_2$, —O—PO(O$^-$)—O—CH$_2$CH$_2$NH$_3$$^+$, -glycoside, —OCH$_3$, —O—CH$_2$—(CHOH)$_4$—CH$_2$OH, —O—CH$_2$—(CHOH)$_2$—CH$_2$OH, —C$_6$H$_3$(OH)$_2$, —NH$^{3+}$, —N$^+$H$_2$R$_b$, —N$^+$HR$_b$R$_c$, or N$^+$HR$_b$R$_c$R$_d$; and wherein each of R, R$_1$, R$_2$, R$_3$, R$_a$, R$_b$, R$_c$ and R$_d$, independently, is C$_{1-30}$ alkyl, each Ar, independently, is aryl, and n is 2–30; or a salt thereof.

Such a salt can be formed between a compound of the above formula and a counterion of an ionizable group of that compound (e.g., sodium, ammonium, and potassium ion are counterions of a carboxyl moiety of that compound). In this disclosure, a fullerene core refers to a caged molecule consisting essentially of carbon atoms such as C$_{60}$, C$_{60}$H$_x$, C$_{70}$, C$_{70}$H$_x$, C$_{76}$, C$_{76}$H$_x$, C$_{78}$, C$_{78}$H$_x$, C$_{82}$, C$_{82}$H$_x$, C$_{84}$, C$_{84}$H$_x$, C$_{92}$, C$_{92}$H$_x$, and the like, in which x is 1–30.

A subset of the derivatives covered by the formula recited above are featured by that each E, independently, is E$_2$, E$_3$, E$_4$, or E$_5$.

Another subset of the derivatives covered by the above formula are featured by that each E, independently, is E$_3$, E$_4$ or E$_5$. Preferably, each X$_1$, independently, is —Y$_1$, —O—Y$_1$, —S—Y$_1$, —NH—Y$_1$, —CO—O—Y$_1$, —CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; each B, independently, is —R$_a$—O—[Si(CH$_3$)$_2$—O—]$_{1-100}$, C$_{6-40}$ aryl, C$_{7-60}$ alkylaryl, C$_{7-60}$ arylalkyl, (C$_{6-40}$ aryl ether)$_{1-100}$, (C$_{7-60}$ alkylaryl ether)$_{1-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$; wherein each of R, R$_a$, R$_1$, R$_2$, and R$_3$, independently, is C$_{1-20}$ alkyl, and each Ar, independently, is aryl; and each D, independently, is —SH, —NHOH, —SO$_3$H, —OSO$_3$H, —CONH$_2$, —CO—NH—NH$_2$, —CH(NH$_2$)—COOH, —P(OH)$_3$, —PO(OH)$_2$, —O—PO(OH)$_2$, —O—PO(OH)—O—PO(OH)$_2$, —O—PO(O)—O—CH$_2$CH$_2$NH$_3$$^+$, -glycoside, —O—CH$_2$—(CHOH)$_4$—CH$_2$OH, —O—CH$_2$—(CHOH)$_2$—CHOH, —C$_6$H$_3$(OH)$_2$, —N$^+$HR$_b$R$_c$, or N$^+$HR$_b$R$_c$R$_d$, wherein each of R, R$_b$, R$_c$, R$_d$, independently, is C$_{1-30}$ alkyl and each Ar, independently, is aryl.

Still another subset of the derivatives covered by the same above formula are featured by that each E, independently, is E$_4$ or E$_5$. Preferably, each X$_1$, independently, is —Y$_1$, —O—Y$_1$, —S—Y$_1$, —NH—Y$_1$, —CO—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; and each of B and D, independently, has the same definition recited above.

Another aspect of this invention features a polyhydroxyorganofullerene derivative of the following formula:

$$F(-E)_n(OH)_m$$

wherein F is a fullerene core; each E, independently, is E$_1$, E$_2$, E$_3$, E$_4$, or E$_5$, in which each E$_{1-5}$ has the same above definition; each of X$_1$ and X$_2$, independently, is —H, —Y$_1$, —O—Y$_1$, —S—Y$_1$, —NH—Y$_1$, —CO—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; each X$_3$, independently, is —Y$_1$, —O—Y$_1$, —S—Y$_1$, —NH—Y$_1$, —C—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; each of Y$_1$, Y$_2$ and Y$_3$, independently, is —B—Z; each B, independently, is —R$_a$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$, (C$_{6-40}$ aryl ether)$_{1-100}$, (C$_{7-60}$ alkylaryl ether)$_{1-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$; each Z, independently, is —C—D—, wherein each C, independently, is —R—, —R—Ar—, —Ar—R—, or —Ar—; and each D, independently, is —OH, —SH, —NH$_2$, —NHOH, —SO$_3$H, —OSO$_3$H, —COOH, —CONH$_2$, —CO—NH—NH$_2$, —CH(NH$_2$)—COOH, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, -glycoside, —OCH$_3$, —O—CH$_2$—(CHOH)$_4$—CH$_2$OH, —O—CH$_2$—(CHOH)$_2$—CHOH, —C$_6$H$_3$(OH)$_2$, —NH$_3^+$, —N$^+$HR$_b$R$_c$, or N$^+$HR$_b$R$_c$R$_d$; wherein each of R, $R_1$, $R_2$, $R_3$, $R_a$, $R_b$, $R_c$, and $R_d$, independently, is $C_{1-30}$ alkyl and each Ar, independently, is aryl; n is 2–30 and m is 1–20; and a salt thereof.

A subset of the derivatives covered by the formula recited above are featured by that each E, independently, is $E_2$, $E_3$, $E_4$, or $E_5$.

Another subset of the derivatives covered by same above formula are featured by that each E, independently, is $E_3$, $E_4$ or $E_5$. Preferably, each $X_1$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; each B, independently, is —$R_a$—O—[Si(CH$_3$)$_2$—O—]$_{1-100}$, $C_{6-40}$ aryl, $C_{7-60}$ alkylaryl, $C_{7-60}$ arylalkyl, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{14-60}$ aryl urethane)$_{1-100}$, ($C_{10-80}$ alkylaryl urethane)$_{1-100}$, ($C_{10-80}$ arylalkyl urethane)$_{1-100}$, ($C_{5-50}$ alkyl urea)$_{1-100}$, ($C_{14-60}$ aryl urea)$_{1-100}$, ($C_{10-80}$ alkylaryl urea)$_{1-100}$, ($C_{10-80}$ arylalkyl urea)$_{1-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{1-100}$, ($C_{7-50}$ aryl carbonate)$_{1-100}$, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$; and each D is independently —SH, —NHOH, —SO$_3$H, —OSO$_3$H, —CONH$_2$, —CO—NH—NH$_2$, —CH(NH$_2$)—COOH, —P(OH)$_3$, —PO(OH)$_2$, —O—PO(OH)$_2$, —O—PO(OH)O—PO(OH)$_2$, —O—PO(O$^-$)—O—CH$_2$CH$_2$NH$_3^+$, -glycoside, —O—CH$_2$—(CHOH)$_4$—CH$_2$OH, —O—CH$_2$—(CHOH)$_2$—CHOH, —C$_6$H$_3$(OH)$_2$, —NH$^+$HR$_b$R$_c$, or N$^+$HR$_b$R$_c$R$_d$, wherein each of R, $R_a$, $R_b$, $R_c$, $R_d$, $R_1$, $R_2$, and $R_3$, independently, is $C_{1-30}$ alkyl and each Ar, independently, is aryl.

Another subset of the derivatives covered by the same above formula are featured by that each E, independently, is $E_4$ or $E_5$. Preferably, each $X_1$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; each of B and D, independently, has the same definition as recited above.

Also within the scope of this invention is a method of preparing a polyorganofullerene derivative of the formula, F—(E)$_n$. The method contains the steps of obtaining a polynitrofullerene or polycyclosulfated fullerene derivative, which acts as a versatile and reactive intermediate, and contacting this intermediate with a nucleophilic agent to afford the polyorganofullerene derivative. In F—(E)$_n$, F is a fullerene core; each E, independently, is $E_1$, $E_2$, $E_3$, $E_4$, $E_5$ or $E_6$, in which each $E_{1-5}$ has the same above definition; and $E_6$, independently, is $Y_1$-amino, $Y_1$-alkoxy, or $Y_1$-thio; each of $X_1$, $X_2$, and $X_3$, independently, is —H, —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; each of $Y_1$, $Y_2$ and $Y_3$, independently, is —H or —B—Z; each B, independently, is —$R_a$—O—[Si(CH$_3$)$_2$—O—]$_{1-100}$, $C_{1-2000}$ alkyl, $C_{6-40}$ aryl, $C_{7-60}$ alkylaryl, $C_{7-60}$ arylalkyl, ($C_{1-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$; each Z, independently, is —C—D—, wherein C, independently, is —R—, —R—Ar—, —Ar—R—, or —Ar—; and D, independently, is —OH, —SH, —NH$_2$, —NHOH, —SO$_3$H, —OSO$_3$H, —COOH, —CONH$_2$, —CO—NH—NH$_2$, —CH(NH$_2$)—COOH, —P(OH)$_3$, —PO(OH)$_2$, —O—PO(OH)$_2$, —O—PO(OH)O—PO(OH)$_2$, —O—PO(O$^-$)—O—CH$_2$CH$_2$NH$_3^+$, -glycoside, —OCH$_3$, —O—CH$_2$—(CH OH)$_4$—CH$_2$OH, —O—CH$_2$—(CHOH)$_2$—CHOH, —C$_6$H$_3$(OH)$_2$, —NH$_3^+$, —N$^+$HR$_b$R$_c$, or —N$^+$HR$_b$R$_c$R$_d$; wherein each of R, R$_1$, R$_2$, R$_3$, R$_a$, R$_b$, R$_c$, and R$_d$, independently, is C$_{1-30}$ alkyl and each Ar, independently, is aryl, and n is 1–30 and m is 1–20; and a salt thereof.

The above-described method can be further extended to produce a polyhydroxyorganofullerene derivative by hydrolyzing the polyorganofullerene derivative thus obtained.

By the term "alkyl" is meant a straight chain that contains 1–30 carbon atoms, or a branched hydrocarbon chain of 3–30 carbon atoms, or cyclic hydrocarbon groups containing 3–30 carbon atoms, or otherwise indicated. These alkyl groups may also contain one or more double bond or triple bond and the cyclic alkyl groups may contain one or more heteroatoms, which are, typically, nitrogen, oxygen, or sulfur. Examples of alkyl groups include, but are not limited to, methyl, ethyl, propyl, isopropyl, butyl, isobutyl, tert-butyl, amyl, pentyl, hexyl, heptyl, octyl, nonyl, decyl, pentadecyl, icosyl, allyl, 2-butenyl, 2-pentenyl, 3-hexenyl, 4-decenyl, 5-nonadecenyl, 2-butnyl, 3-octnyl, 5-octadecnyl, cyclopropyl, cyclopentyl, cyclohexyl, cycloheptyl, adamantyl, norbornyl, isobornyl, cyclopentylmethyl, cyclohexylmethyl, 1- or 2-cyclohexylethyl, cyclopentenyl, cyclohexenyl, cycloheptenyl, cyclo-octenyl, tetrahydrofuranyl, tetrahydropyranyl, piperidinyl, morpholino and pyrrolindinyl groups.

As used herein, the term "aryl" refers to C$_{6-40}$ aromatic rings. These moieties may also be fused rings and can be fused with aryl or heteroaryl which is as defined below. Fused rings are rings that share a common carbon—carbon bond. Typically aryl groups include phenyl, naphthyl, biphenyl, indazolyl, phenanthryl, and anthracyl.

By the term "heteroaryl" in this disclosure is meant C$_{6-40}$ aromatic rings that contain one or more heteroatoms as defined above. These moieties may also be fused rings. Examples of heteroaryl groups include pyridyl, pyrazinyl, pyrimidyl, furyl, pyrrolyl, thienyl, thiazolyl, oxazolyl, imidazolyl, coumarinyl, indolyl, benzofuranyl, benzthiazolyl, benzothienyl, and benzothiadiazolyl.

As used herein, the term "halide" is defined as fluoro, chloro, bromo, or iodo. The terms "polynitrofullerenes" and "polycyclosulfated fullerenes" in this disclosure have the formulas, F—(NO$_2$)$_n$ and F—(SO$_4$)$_n$, respectively, in which n is at least 2. The term "nucleophilic agent" is defined as an electron-rich species that donates electrons in a reaction. Examples of nucleophilic agents that can be employed in the preparation of polyorganofullerene derivatives include amine, phenol, alkoxide, organothiolate, carbanion, organoamide anion, thiol, amino acid, and thiol carbamate anion. Note that the just-mentioned nucleophilic agents can be unsubstituted or substituted with other functional groups. Examples of substituted nucleophilic agents include 1,4-naphthoquinonylamine, tyrosine, dihydroxypropylthiol, and the like. For instance, polynitrofullerene can react with the nucleophilic agent dihydroxypropylthiol to produce the corresponding polyorganofullerene derivative poly (dihydroxypropylmercapto)fullerene. See example 19 below. By the term "hydrolysis" is meant a water molecule, under basic or acidic condition, attacks and breaks a susceptible bond of a compound. Bases are generally employed as hydrolyzing agents herein for the preparation of polyhydroxyorganofullerene derivatives and sodium hydroxide is a preferred hydrolyzing agent in this disclosure.

The structures of many of the moieties mentioned above are shown below within the pair of parentheses following each of the moieties: alkyl ether (—R—O—), aryl ether (—Ar—O—), alkylaryl ether (—R—Ar—O—), arylalkyl ether (—Ar—R—O—), alkyl thioether (—R—S—), aryl thioether (—Ar—S—), alkylaryl thioether (—R—Ar—S—), arylalkyl thioether (Ar—R—S—), alkyl ester (—R—O—CO—, —R—CO—O—, —R$_1$—CO—O—R$_2$—O—CO—, or —R$_1$—O—CO—R$_2$—CO—O—), aryl ester (—Ar—O—CO—, —Ar—CO—O, Ar—CO—O—Ar$_2$—O—CO—, or —Ar$_1$—O—CO—Ar$_2$—CO—O—), alkylaryl ester (—R—Ar—O—CO— or —R—Ar—CO—O—), arylalkyl ester (—Ar—R—O—CO or —Ar—R—CO—O—), alkyl urethane (—R$_1$—O—CO—NH—R$_2$—NH—CO—O—), aryl urethane (—Ar$_1$—O—CO—NH—Ar$_2$—NH—CO—O—), alkylaryl urethane (—R$_1$—Ar—O—CO—NH—R$_2$—NH—CO—O—, —R—Ar$_1$—O—CO—

NH—Ar$_2$—NHCO—O—, or —R$_1$—O—CO—NH—Ar—R$_2$—Ar—NH—CO—O—), arylalkyl urethane (—Ar—R$_1$—O—CO—NH—R$_2$—NH—CO—O—, —Ar$_1$—R—O—CO—NH—Ar$_2$—NH—CO—O—, or —Ar$_1$—O—CO—NH—Ar$_2$—R—Ar$_2$—NH—CO—O—), alkyl urea (—R$_1$—NH—CO—NH—R$_2$NH—CO—NH—), aryl urea (—Ar$_1$—NH—CO—NH—Ar$_2$—NH—CO—NH—), alkylaryl urea (—R$_1$—Ar—NH—CO—NH—R$_2$—NH—CO—NH—, —R—Ar—NH—CONH—Ar$_2$—NH—CO—NH—, or —R$_1$—NH—CO—NH—Ar—R$_2$—Ar—NH—CO—NH—), arylalkyl urea (—Ar—R$_1$—NH—CO—NH—R$_2$—NH—CO—NH—, —Ar$_1$—R—NH—CONH—Ar$_2$—NH—CO—NH—, or —Ar$_1$—NH—CO—NH—Ar$_2$—R—Ar$_2$—NH—CO—NH—), alkyl amide (—R—NH—CO—, —R—CO—NH—, —R$_1$—CO—NH—R$_2$—NH—CO—, or —R$_1$—NH—CO—R$_2$—CO—NH—), aryl amide (—Ar—NH—CO—, —Ar—CO—NH—, Ar$_1$—CO—NH—Ar$_2$—NH—CO—, or —Ar$_1$—NH—CO—Ar$_2$—CO—NH—), alkylaryl amide (—R—Ar—NH—CO—, —R—CO—NH—Ar—NH—CO—, or —R—NH—CO—Ar—CONH—), arylalkyl amide (—Ar—R—NH—CO—, —Ar—CO—NH—R—NH—CO—, or —Ar—NH—CO—R—CO—NH—), alkyl anhydride (—R—CO—O—CO—), aryl anhydride (—Ar—CO—O—CO—), alkylaryl anhydride (—R—Ar—CO—O—CO— or —R—CO—O—CO—Ar—CO—O—CO—), arylalkyl anhydride (—Ar—R—O—O—CO— or —Ar—CO—O—CO—R—CO—O—CO—), alkyl carbonate (—R—OCO—O—), aryl carbonate (—Ar—O—CO—O—), alkylaryl carbonate (R—Ar—O—CO—O— or —R—O—CO—O—Ar—O—CO—O—), and arylalkyl carbonate (—Ar—R—O—CO—O— or —Ar—O—CO—O—R—O—CO—O—). Note that the di-substitution pattern on Ar can be para, meta, or ortho.

One can employ polynitrofullerenes, F—(NO$_2$)$_n$, or polycyclosulfated fullerenes, F—(SO$_4$)$_n$, described herein as intermediates for preparation of various polyorganofullerene derivatives (as shown in the following examples). The use of these intermediates allows the reactions to proceed at a fast rate under a mild condition. These fullerene derivatives that are synthesized from polynitrofullerenes or polycyclosulfated fullerenes can, in turn, be used to produce fullerene-grafted polymers. See U.S. Pat. No. 5,635,581. In addition to acting as starting materials for polymers, these derivatives have also been demonstrated to be useful free-radicals scavengers. See U.S. Pat. No. 5,648,523.

Other features and advantages of the present invention will be apparent from the following description of the preferred embodiments, and also from the appending claims.

DETAILED DESCRIPTION OF THE INVENTION

Described below are various methods for synthesizing some of the polyorganofullerene derivatives via polynitrofullerenes or polycyclosulfated fullerenes described herein. Polynitrofullerene derivatives, F—(NO$_2$)$_n$, which act as a reactive intermediate in this invention, can be prepared by one of the following methods:

a) A method for producing F—(NO$_2$)$_n$ involve reacting fullerene, F, with nitrogen dioxide radicals, NO$_2$·, which are generated from sodium nitrite, NaNO$_2$, and concentrated HNO$_3$. See Chiang et al., Tetrahedron 1996, 52(14), 4963. The structure of F—(NO$_2$)$_n$ has been characterized to contain at least 4 nitro groups.

b) F—(NO$_2$)$_n$, wherein n is 4, can also be prepared from reacting fullerene with dinitrogen tetraoxide, N$_2$O$_4$ in carbon disulfide solution. See Cataldo et al., Fullerene Sci. & Techno. 1997, 5(1), 257.

c) Yet another method for the preparation of F—(NO$_2$)$_n$ can be done by reacting fullerene with nitrogen dioxide gas, which is generated from a mixture of NaNO$_2$ and FeSO$_4$ in aqueous H$_2$SO$_4$. See Sarkar et al., J. Chem. Soc., Chem. Commum. 1994, 275.

d) Still another method for the preparation of F—(NO$_2$)$_n$ can be done by reacting fullerene with fuming nitric acid. See Hamwi et al., Fullerene Sci. & Techno. 1996, 4(5), 835.

Polycyclosulfated fullerene derivatives, F—(SO$_4$)$_n$, which can also be employed as an effective intermediate in this invention, can be prepared by reacting fullerene and neat fuming sulfuric acid in the presence of an oxidant (e.g., P$_2$O$_5$, V$_2$O$_5$, or SeO$_2$). The structure of the product has been characterized to consist at least 4 cyclosulfated units.

Polyorganofullerene derivatives, F—(E)$_n$, can be synthesized in general by reacting F—(NO$_2$)$_n$ or F—(SO$_4$)$_n$ with a nucleophilic agent, E—H, (e.g., primary and secondary organoamino compound, alkoxide, organothiolate, organophenol compound, carbanion, organoamide anion, thiocarbamate ion, and the like) in a non-reactive solvent, such as tetrahydrofuran. A base may be needed in some reactions (see examples below) to produce a nucleophilic anion of E—H that is of enough strength to undergo the substitution reaction. Some examples of such a base include 1,8-diazabicyclo[5.4.0]-undec-7-ene (DBU), 1,5-diazabiacyc[4.3.0]non-5-ene (DBU), and lithium diisopropyl-amine (LDA).

Alternatively, F—(E)$_n$ can be prepared by reacting F—(NO$_2$)$_n$ or F—(SO$_4$)$_n$ with a lithium salt of E—H, which is generated by reacting E—H with lithium triethylborohydride (Super-Hydride®) in tetrahydrofuran or other non-reactive solvents. Examples of lithium salts of E—H include, but are not limited to, lithium organoamino compounds, lithium organothiolate, lithium organophenol.

A polyorganofullerene derivative from the reactions set forth above, F—(E)$_n$, can further react with a hydrolyzing agent to generate a polyhydroxyorganofullerene derivative, F—(E)$_n$(OH)$_m$. For instance, sodium hydroxide is an effective hydrolyzing agent in this disclosure and tetrabutylammonium hydroxide can be used herein as a phase-transfer agent. Note that the symbol, n, used in each term does not necessary have the same number as the same symbol used in another term in this disclosure.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All publications recited herein, including patents, are hereby incorporated by reference in their entirety.

EXAMPLE 1

Preparation of Polynitro-fullerenes, C$_{60}$(NO$_2$)$_n$

A two-necked reaction flask A (50 ml) was equipped with a vertical dropping funnel with a stopcock on one neck and a connecting gas bubbling tube on the other neck. The gas-bubbling tube was attached with a drying tube (CaCl$_2$) and inserted into the second two-necked reaction flask B. The other neck of flask B was attached with a bubbling tube which was extended into a trapping flask containing aqueous sodium hydroxide solution (2 N). To minimize the back-flow of moisture from alkaline solution, a drying tube (CaCl$_2$) was installed in between the flask B and the trapping flask. A steady inert gas (N$_2$) flow was allowed starting from the top of dropping funnel, through the reaction flasks A and B in sequence, into the alkaline solution in the trapping flask. The dropping funnel and the reaction flask A were charged with conc. $HNO_3$ (10 ml) and copper powder (10 g), respectively. In the reaction flask B was placed a solution of [60]fullerene (500 mg) in benzene (50 ml, dried over Na). The inert gas bubbling through the $C_{60}$ solution in the flask B was adjusted to a flow rate of 5 ml per min. The fullerene solution was deoxygenated for at least 5 min prior to the reaction. Conc. $HNO_3$ solution was then allowed to add dropwise into sodium nitrite solids in the flask A. Brown fume was produced immediately upon the contact of conc. $HNO_3$ with $NaNO_2$. It was carried by the steady flow of $N_2$ and bubbled through the $C_{60}$ solution in the flask B. Within 15 min of reaction, the purple solution of $C_{60}$ was changed to orange-red progressively. The mixture was stirred at ambient temperature for an additional 2 h to give a dark brown-red solution with suspended solids. At the end of reaction, excessive nitrogen dioxide ($NO_2$) was removed by $N_2$ bubbling and destroyed in the trapping solution. Benzene was then evaporated from the product solution at a reduced pressure to give dark brown solids. The solids were suspended in anhydrous n-hexane, separated from n-hexane solution by the centrifuge technique and dried in vacuum at 40° C. to afford brown solids of polynitrofullerene derivatives, $C_{60}(NO_2)_n$ (n=4–6 on average) (650 mg). $IRv_{max}$ (KBr) 1572 [s, $v_{as}$(N—O)], 1328 [s, $v_s$(N—O)], 1085, 1038, 973, 815 (δ), 760, 733, 696, 545, and 466 $cm^{-1}$. The product exhibits appreciable solubility in common organic solvents such as THF, DMF, $CH_2Cl_2$, $CH_3OH$ and DMSO.

EXAMPLE 2

Synthesis of Polycyclosulfated Fullerenes, $C_{60}(SO_4)_n$

A reaction flask (50 ml) charged with a fullerene mixture of $C_{60}$ (80%) and $C_{70}$ (20%) (1.0 g), an oxidant, and fuming sulfuric acid (15 ml) was stirred at 55–60° C. under $N_2$ for 5 min to 3 h to give a light brown solution with orange suspensions. The oxidant can be selected from either $P_2O_5$ (6.0 g), $V_2O_5$ (150 mg), or $SeO_2$ (700 mg). The resulting mixture was added dropwise into cold ice-water (200 ml) to cause the precipitation of products. Precipitates were separated from the aqueous solution by the centrifuge technique. They were then washed and centrifuged twice with cold ice-water and dried in vacuum at 40° C. to afford brown-orange solids of polycyclosulfated fullerenes, $C_{60}(SO_4)_n$, (1.4 g). The physical data of $C_{60}(SO_4)_n$ are as follow: $IRv_{max}$ (KBr) 2920 (br), 2400 (br), 1706 (w), 1654 (w), 1598 (w), 1427 (s), 1229 (s), 1168, 1046, 1002 (s), 981, 953 (s), 855, 826 (s), 783, 641, 530, 485 (w), and 411 (w) $cm^{-1}$; $^{13}C$ NMR (DMF-$d_7$, peak center) δ 148.0, 77.0, 71.0; $^1H$ NMR (DMF-$d_7$, peak center) δ 14.6 (w, $OSO_2$—OH of a partially hydrolyzed product).

EXAMPLE 3

Synthesis of Polyaminofullerenes, $C_{60}(NH_2)_m$—Method 1

A round-bottom reaction flask (100 ml) equipped with a magnetic stirrer was fitted with a septum and a cool-trap condenser. It was charged with $C_{60}(NO_2)_n$ (500 mg) and tetrahydrofuran (40 ml). The solution was slowly bubbled with a stream of $NH_3$ gas (5 ml per min) at ambient temperature for 2 h with dry-ice/acetone filling in the cool-trap. At the end of reaction, the resulting solution was added methanol (60 ml) to effect precipitation of brown solids. The solid precipitate was isolated by a centrifuge technique. It was then washed twice with methanol (20 ml each time) and dried in vacuum at 40° C. to afford brown solid of the corresponding polyaminofullerene derivative $C_{60}(NH_2)_m$ (m≧n). Increase of number of substituents is due to further nucleophilic additions of $NH_3$ on polyaminated fullerenes. The physical data of polyamino fullerenes are as follows: $IRv_{max}$ (KBr) 3400 (s, $NH_2$), 3246 (s), 1625, 1556, 1387, 1347, 1271, 1058, 742, and 545 $cm^{-1}$.

EXAMPLE 4

Synthesis of Polyaminofullerenes, $C_{60}(NH_2)_m$—Method 2

A round-bottom reaction flask (100 ml) equipped with a magnetic stirrer was fitted with a septum and a cool-trap condenser. It was charged with $C_{60}(NO_2)_n$ (500 mg) and tetrahydrofuran (30 ml). The solution was added $NaNH_2$ (400 mg) and stirred at ambient temperature for 3 h. At the end of reaction, the resulting solution was added methanol (60 ml) to effect precipitation of brown solids. The solid precipitate was isolated by a centrifuge technique. It was then washed twice with methanol (20 ml each time) and dried in vacuum at 40° C. to afford brown solid of the corresponding polyamino-fullerene derivatives, $C_{60}(NH_2)_m$, (m≧n). Increase of number of substituents is due to further nucleophilic additions of $NH_3$ on polyaminated fullerenes. The physical data of polyamino fullerenes are as follows: $IRv_{max}$ (KBr) 3388 (s, $NH_2$), 3269 (s), 1637, 1557, 1381, 1346, 1271, 1060, 669, and 538 $cm^{-1}$.

EXAMPLE 5

Synthesis of Polyaminofullerenes—Method 3

A round-bottom reaction flask A (100 ml) equipped with a magnetic stirrer was fitted with a septum and purged with $N_2$. It was charged with $C_{60}(NO_2)_n$ (500 mg) and tetrahydrofuran (30 ml). In a separated reaction flask B, benzamide (1.1 equiv. of halogen group in halogenated fullerene) was allowed to react with sodium hydride (1.1. equiv. of benzamide) in tetrahydrofuran (20 ml, distilled over Na) at ambient temperatures to afford immediately the corresponding solution of sodium benzamide ($C_6H_5$CONHNa). The solution was added portionwise into the reaction flask A at 0° C. and the mixture was stirred further at that temperature for an additional 3 h. At the end of reaction, all solvents were removed from the resulting solution in vacuum to give brown solids. These solids were transferred into an aqueous solution of NaOH (15 ml, 3 N) and the mixture was stirred and heated at 90° C. for 16 h. It was cooled to ambient temperature and added methanol (60 ml) to cause precipitation of dark brown solids. The solid precipitate was isolated by a centrifuge technique. It was then washed twice with methanol (20 ml each time) and dried in vacuum at 40° C. to afford brown solids of the corresponding polyaminofullerene derivative, $C_{60}(NH_2)_n$.

EXAMPLE 6

Synthesis of Polyaminofullerenes, $C_{60}(NH_2)_m$—Method 4

A round-bottom reaction flask (100 ml) equipped with a magnetic stirrer was fitted with a septum and a cool-trap condenser. It was charged with $C_{60}(SO_4)_n$ (500 mg) and tetrahydrofuran (40 ml). The solution was slowly bubbled with a stream of $NH_3$ gas (5 ml per min) at ambient temperature for 2 h with dry-ice/acetone filling in the cool-trap. At the end of reaction, the resulting solution was added methanol (60 ml) to effect precipitation of brown solids. The solid precipitate was isolated by the centrifuge technique. It was then washed twice with methanol (20 ml each time) and dried in vacuum at 40° C. to afford brown solid of the corresponding polyamino fullerene derivative $C_{60}(NH_2)_m$ (m≧n). The physical data of polyamino fullerenes are as follows: $IRv_{max}$ (KBr) 3400 (s, $NH_2$), 3246 (s), 1625, 1556, 1387, 1347, 1271, 1058, 742, and 545 $cm^{-1}$.

EXAMPLE 7

Synthesis of Poly(diethanolamino)fullerenes, $C_{60}[-N(CH_2CH_2OH)_2]_n$

A round-bottom reaction flask (100 ml) equipped with a magnetic stirrer was fitted with a septum and a cool-trap condenser. It was charged with $C_{60}(NO_2)_n$ (500 mg) and acetone (30 ml). The solution was added diethanolamine (distilled, 900 mg) in acetone (30 ml) and stirred at ambient temperatures for 12 h. At the end of reaction, suspended solids in the solution were separated by a centrifuge technique and repeatedly washed with acetone and tetrahydrofuran. The resulting brown solids were dried in vacuum at 40° C. to afford the corresponding poly(diethanolamino) fullerenes (535 mg). The physical data of poly (diethanolamino)fullerenes are as follows: $IRv_{max}$ (KBr) 3374 (s, OH), 2933 (C—H), 1650, 1565, 1453, 1387, 1268, 1070, 669, and 538 $cm^{-1}$. $^1H$ NMR (300 MHz, DMSO-$d_6$) δ 3.0 (triplet, $CH_2$), 3.32 (OH), 3.63 (triplet, $CH_2$), and 4.56.

EXAMPLE 8

Synthesis of Poly(diethanolamino)fullerenes, $C_{60}[-N(CH_2CH_2OH)_2]_n$

A round-bottom reaction flask (100 ml) equipped with a magnetic stirrer was fitted with a septum and a cool-trap condenser. It was charged with $C_{60}(SO_4)_n$ (500 mg) and tetrahydrofuran (30 ml). The solution was added diethanolamine (distilled, 900 mg) in tetrahydrofuran (30 ml) and stirred at ambient temperatures for 5 h. At the end of reaction, suspended solids in the solution were separated by the centrifuge technique and repeatedly washed with acetone. The resulting brown solids were dried in vacuum at 40° C. to afford the corresponding poly(diethanolamino) fullerenes (520 mg). The physical data of poly (diethanolamino)fullerenes are as follows: $IRv_{max}$ (KBr) 3374 (s, OH), 2933 (C—H), 1650, 1565, 1453, 1387, 1268, 1070, 669, and 538 $cm^{-1}$. $^1H$ NMR (300 MHz, DMSO-$d_6$) δ 3.0 (triplet, $CH_2$), 3.32 (OH), 3.63 (triplet, $CH_2$), and 4.56.

EXAMPLE 9

Synthesis of Poly(hydroxyethoxyethylamino) fullerenes, $C_{60}(-NHCH_2CH_2OCH_2CH_2OH)_n$ A round-bottom reaction flask (100 ml) equipped with a magnetic stirrer was fitted with a septum and a cool-trap condenser. It was charged with $C_{60}(NO_2)_n$ (500 mg) and tetrahydrofuran (30 ml). The solution was added tris (hydroxymethyl)-methylamine (900 mg) in tetrahydrofuran (30 ml) and stirred at ambient temperatures for 16 h. At the end of reaction, suspended solids in the solution were separated by a centrifuge technique and repeatedly washed with tetra-hydrofuran and acetone. The resulting brown solids were dried in vacuum at 40° C. to afford the corresponding poly(hydroxy-ethoxyethylamino)fullerenes (490 mg). The physical data of poly(hydroxyethoxyethylamino) fullerenes are as follows: $IRv_{max}$ (KBr) 3381 (s, OH), 2933 (C—H), 2868 (C—H), 1644, 1565, 1453, 1354, 1242, 1117 (s), 1065 (s), and 531 $cm^1$. $^1H$ NMR (300 MHz, DMSO-$d_6$) δ 2.9 (m, $CH_2$), 3.32 (OH), and 3.62 (m, $CH_2$)

EXAMPLE 10

Synthesis of Poly[tris(hydroxymethyl)methylamino] fullerenes, $C_{60}[-NHC-(CH_2OH)_3]_n$ A round-bottom reaction flask (100 ml) equipped with a magnetic stirrer was fitted with a septum and a cool-trap condenser. It was charged with $C_{60}(NO_2)_n$ (500 mg) and tetrahydrofuran (30 ml). The solution was added tris (hydroxymethyl)methylamine (900 mg) in tetrahydrofuran (30 ml) and stirred at ambient temperatures for 24 h. At the end of reaction, suspended solids in the solution were separated by a centrifuge technique and repeatedly washed with tetrahydrofuran and acetone. The resulting brown solids were dried in vacuum at 40° C. to afford the corresponding poly[tris(hydroxymethyl)methylamino]fullerenes (570 mg), which is soluble in dimethylformamide. The physical data of poly[tris(hydroxymethyl)methylamino]fullerenes are as follows: $IRv_{max}$ (KBr) 3400 (s, OH), 2935 (C—H), 2870 (C—H), 1640, 1565, 1454, 1354, 1067 (s), and 582 $cm^{-1}$. $^1H$ NMR (200 MHz, DMSO-$d_6$) δ 2.91 ($CH_2O$) and 3.75 (OH).

EXAMPLE 11

Synthesis of Poly(disuccinyloxyethylamino) fullerenes, $C_{60}[-N(CH_2CH_2OCOCH_2CH_2CO_2H)_2]_n$ A round-bottom reaction flask (100 ml) equipped with a magnetic stirrer was fitted with a septum and a cool-trap condenser. It was charged with succinic anhydride (250 mg), p-toluenesulfonic acid (5 mg), and benzene (25 ml). The mixture was added poly(diethanolamino)fullerenes, $C_{60}[-N(CH_2CH_2OH)_2]_n$, (200 mg) and stirred at 75° C. for 2 h. At the end of reaction, suspended solids in the solution were separated by a centrifuge technique and repeatedly washed with hot benzene. The resulting brown solids were dried in vacuum at 40° C. to afford the corresponding poly (disuccinyloxyethyl-amino)fullerenes, $C_{60}[-N(CH_2CH_2OCOCH_2CH_2CO_2H)_2]_n$ (210 mg). The physical data of poly(disuccinyloxyethylamino)fullerenes are as follows: $IRv_{max}$ (KBr) 3420 (s), 2933 (C—H), 2644, 2545 ($CO_2H$), 1729 (s, C=O), 1637, 1413, 1308,, 1209, 1170, 1078, 1012, 913, 801, 689, 637, and 564 $cm^{-1}$.

EXAMPLE 12

Synthesis of Poly(p-methylphenylamino)fullerenes, $C_{60}[-NHC_6H_5CH_3]_n$

A round-bottom reaction flask (100 ml) equipped with a magnetic stirrer was fitted with a septum and a cool-trap condenser. It was charged with $C_{60}(NO_2)_n$ (400 mg) and tetrahydrofuran (30 ml). The solution was added 4-methylaniline (500 mg) in tetrahydrofuran (10 ml) and treated under sonication conditions for 25 min at ambient temperatures. At the end of reaction, all solvents in the solution were removed via vaccuo. The resulting semi-solids were redissolved in benzene, precipitated from hexane, and washed with hexane. These brown solids were dried in vacuum at 40° C. to afford the corresponding poly(p- methylphenylamino)fullerenes, $C_{60}[-NHC_6H_5CH_3]_n$, (450 mg), which is soluble in benzene. The physical data of poly(p-methylphenylamino) fullerenes are as follows: $IRv_{max}$ (KBr) 3347, 3381 (s), 3039 (C—H), 1604 (s), 1565, 1499 (s), 1380, 1341, 1308, 1249, 1117, 1058, 1031, 755 (s), 696 (s), and 505 $cm^{-1}$.

EXAMPLE 13

Synthesis of Poly(N-phenyl-1,4-phenylenediamino) fullerenes, $C_{60}[-NHC_6H_4NHC_6H_5]_n$ A round-bottom reaction flask (100 ml) equipped with a magnetic stirrer was fitted with a septum and a cool-trap condenser. It was charged with $C_{60}(NO_2)_n$ (400 mg) and tetrahydrofuran (30 ml). The solution was added N-phenyl-1,4-phenylenediamine (500 mg, $NH_2C_6H_4NHC_6H_5$) in tetrahydrofuran (10 ml) and treated under sonication conditions for 25 min at ambient temperatures. At the end of reaction, the resulting precipitates were separated by filtration and washed repeatedly with methylene chloride. The solids were redissolved in dimethylformamide, precipitated from a mixture of acetone and hexane, and washed with acetone. The light green solids were then dried in vacuum at 40° C. to afford the corresponding poly(N-phenyl-1,4-phenylenediamino)fullerenes, $C_{60}[-NHC_6H_4NHC_6H_5]_n$, (380 mg). The physical data of poly(N-phenyl-1,4-phenylenediamino)fullerenes are as follows: $IRv_{max}$ (KBr) 3394 (N—H), 3045, 2914, 1598, 1571 (s), 1512 (s), 1495 (s), 1453 (w), 1328 (s), 1249 (w), 1170, 1117, 1071, 808, 748, 689, and 498 $cm^{-1}$.

EXAMPLE 14

Synthesis of Poly(phenylamino)fullerenes, $C_{60}[-NHC_6H_5]_n$

A round-bottom reaction flask (100 ml) equipped with a magnetic stirrer was fitted with a septum and a cool-trap condenser. It was charged with $C_{60}(NO_2)_n$ or $C_{60}(SO_4)_n$ (400 mg) and tetrahydrofuran (30 ml). The solution was added aniline or lithium aluminum anilinide (LiAl(HN—$C_6H_5)_4$) (500 mg) in tetrahydrofuran (10 ml) and treated under sonication conditions for 25 min at ambient temperatures. At the end of reaction, all solvents in the solution were removed via vaccuo. The resulting semi-solids were redissolved in benzene, precipitated from hexane, and washed with hexane. These brown solids were dried in vacuum at 40° C. to afford the corresponding poly(phenylamino) fullerenes, $C_{60}[-NHC_6H_5]_n$, (445 mg), which is soluble in benzene. The physical data of poly(phenylamino)fullerenes are as follows: $IRv_{max}$ (KBr) 3447, 3381, 3039, 1604 (s), 1565, 1499 (s), 1380, 1341, 1308, 1249, 1117, 1058, 1032, 894, 755 (s), 696 (s), 545, and 505 $cm^{-1}$.

EXAMPLE 15

Synthesis of Poly[N,N'-bis(4'-aminophenyl)-1,4-quinonenediimino] fullerenes, $C_{60}[-NH-C_6H_4-N=C_6H_4=N-C_6H_4-NH_2]_n$ A round-bottom reaction flask (100 ml) equipped with a magnetic stirrer was fitted with a septum and a cool-trap condenser. It was charged with $C_{60}(NO_2)_n$ (400 mg) and tetrahydrofuran (30 ml). The solution was added N,N'-bis (4'-aminophenyl)-1,4-quinonenediimine (500 mg, $NH_2-C_6H_4-N=C_6H_4=N-C_6H_4-NH_2$) in tetrahydrofuran (10 ml) with or without 1,8-diazabicyclo[5.4.0]undec-7-ene (DBU, 500 mg) and treated under sonication conditions for 25 min at ambient temperatures. At the end of reaction, the resulting precipitates were separated by filtration and washed repeatedly with methylene chloride. The solids were redissolved in dimethylformamide, precipitated from a mixture of acetone and hexane, and washed with acetone. The dark green solids were then dried in vacuum at 40° C. to afford the corresponding poly[N,N'-bis(4'-aminophenyl)-1,4-quinonene-diimino] fullerenes, $C_{60}[-NH-C_6H_4-N=C_6H_4=N-C_6H_4-NH_2]_n$, (380 mg). The physical data of poly[N,N'-bis(4'-aminophenyl)-1,4-quinonenediimino] fullerenes are as follows: $IRv_{max}$ (KBr) 3434, 2927 (C—H), 2872, 1604 (s) 1591 (s), 1501 (s), 1341 (s), 1150 (s), 1047, 834, 732, 552, and 464 $cm^{-1}$.

EXAMPLE 16

Synthesis of 4-Aminobenzylphosphonic Acid Derivatives of $C_{60}$, $C_{60}[-NHC_6H_4CH_2P(=O)(OH)_3]_n$ A round-bottom reaction flask (25 ml) equipped with a magnetic stirrer was fitted with a septum and a cool-trap condenser. It was charged with $C_{60}(NO_2)$ (100 mg) and tetrahydrofuran (15 ml). The solution was added 4-aminobenzylphosphonic acid (150 mg) in tetrahydrofuran (5 ml) and treated under sonication conditions for 30 min at ambient temperatures. At the end of reaction, suspended solids in the solution were separated by a centrifuge technique and repeatedly washed with tetrahydrofuran and acetone. The resulting brown solids were dried in vacuum at 40° C. to afford the corresponding 4-aminobenzylphosphonic acid derivatives of $C_{60}$, $C_{60}[-NHC_6H_4CH_2P(=O)(OH)_3]_n$, (95 mg) and 1,8-diazabicyclo[5.4.0]undec-7-ene (DBU, 400 mg).

EXAMPLE 17

Synthesis of Amino Acid Derivatives of $C_{60}$, Poly (L-tyrosinated)fullerenes, $C_{60}[-OC_6H_4CH_2CH(NH_2)CO_2H]_n$ To a solution of $C_{60}(NO_2)_n$ (300 mg) in tetrahydrofuran (50 ml) in a round-bottom reaction flask was added L-tyrosine (500 mg, finely divided) and 1,8-diazabicyclo [5.4.0]undec-7-ene (DBU, 600 mg). The mixture was stirred at 45° C. for a period of 16 h to give a dark reddish brown solid suspended solution. The suspended solids in the solution were separated by a centrifuge technique and repeatedly washed with tetrahydrofuran, dimethylformamide, and acetone in sequence. The resulting brown solids were dried in vacuum at 40° C. to afford the corresponding poly(L-tyrosinated) fullerenes, $C_{60}[-OC_6H_4CH_2CH(NH_2)CO_2H]_n$, (410 mg). The physical data of poly(L-tyrosinated) fullerenes are as follows: $IRv_{max}$(KBr) 3415 (s), 3200, 2900 (C—H), 2580 (br, $CO_2H$), 1592 (s), 1580, 1557, 1473, 1400, 1384, 1326, 1300, 1202, 1070 (br, s), 814, 785, 703, 635, 587, and 514 $cm^{-1}$.

EXAMPLE 18

Synthesis of 2-Hydroxymethylphenol Derivatives of $C_{60}$, $C_{60}[-OC_6H_4CH_2OH]_n$ To a solution of $C_{60}(SO_4)_n$ (300 mg) in tetrahydrofuran (50 ml) in a round-bottom reaction flask was added 2-hydroxymethylphenol (1.0 g) with or without 1,8-diazabicyclo[5.4.0]undec-7-ene (DBU, 400 mg). The mixture was stirred at 50° C. for a period of 1.5 h to give a dark reddish brown solid suspended solution. The suspended solids in the solution were separated by a centrifuge technique and repeatedly washed with water. The resulting brown solids were dried in vacuum at 40° C. to afford the corresponding 2-hydroxymethylphenol derivatives of fullerene, $C_{60}[-OC_6H_4CH_2OH]_n$, (410 mg). The products are soluble in tetrahydrofuran. The physical data of 2-hydroxymethylphenol derivatives of fullerene are as follows: $IRv_{max}$ (KBr) 3375 (s, broad), 2928 (C—H), 1649, 1611, 1593, 1500, 1455, 1382, 1228, 1057 (s), 843, 753, and 526 cm$^{-1}$.

EXAMPLE 19

Synthesis of Poly(2,3-dihydroxypropylmercapto) fullerenes, $C_{60}(-SCH_2CH(OH)CH_2OH)_n$ A round-bottom reaction flask (100 ml) equipped with a magnetic stirrer was fitted with a septum and a cool-trap condenser. It was charged with $C_{60}(NO_2)_n$ (350 mg) and tetrahydrofuran (20 ml). The solution was added 2,3-dihydroxypropylthiol (500 mg), 1,8-diazabicyclo[5.4.0] undec-7-ene (DBU, 500 mg), and triethylamine (1 g) in methylene chloride (20 ml) and stirred at 60° C. for 10 h. At the end of reaction, all solvents in the solution were removed via vaccuo to obtain gummy products. The resulting semi-solids were suspended in ethylacetate to yield brown solids, which were washed with ethylacetate. These brown solids were dried in vacuum at 40° C. to afford the corresponding poly(2,3-dihydroxypropylmercapto)fullerenes, $C_{60}(-SCH_2CH (OH) CH_2OH)_n$, (315 mg). The physical data of poly(2,3-dihydroxy-propylmercapto)fullerenes are as follows: $IRv_{max}$ (KBr) 3400 (s, OH), 2920 (C—H), 2868 (C—H), 1621, 1400, 1157, 1046, 1025, 652, 574, and 511 cm$^{-1}$.

EXAMPLE 20

Synthesis of Mercaptosuccinic Acid Derivatives of Fullerenes, $C_{60}[-SCH_2(CO_2H) CH_2CO_2H]_n$ A round-bottom reaction flask (100 ml) equipped with a magnetic stirrer was fitted with a septum and a cool-trap condenser. It was charged with $C_{60}(NO_2)_n$ (400 mg), triethylamine (1 g), and tetrahydrofuran (25 ml). The solution was added 2-mercaptosuccinic acid (550 mg) and 1,8-diazabicyclo[5.4.0]undec-7-ene (DBU, 600 mg) in tetrahydrofuran (25 ml) and stirred at 60° for 10 h. At the end of reaction, suspended solids in the solution were separated by a centrifuge technique and repeatedly washed with tetrahydrofuran. The resulting brown solids were dried in vacuum at 40° C. to afford the corresponding mercaptosuccinic acid derivatives of fullerenes, $C_{60}[-SCH_2(CO_2H)CH_2CO_2H]_n$, (405 mg). The physical data of these compounds are as follows: $IRv_{max}$ (KBr) 3425 (s, OH), 2910 (C—H), 2608–2534 (CO$_2$H), 1700 (s), 1623, 1544, 1392, 1388, 1307, 1263, 1202, 1173, 1056, and 525 cm$^{-1}$.

EXAMPLE 21

Synthesis of Mercaptosuccinic Acid Derivatives of Fullerenes, $C_{60}[-SCH_2(CO_2H)CH_2CO_2H]_n$ A round-bottom reaction flask (100 ml) equipped with a magnetic stirrer was fitted with a septum and a cool-trap condenser. It was charged with $C_{60}(SO_4)_n$ (400 mg) and tetrahydrofuran (25 ml). The solution was added 2-mercaptosuccinic acid (550 mg) in tetrahydrofuran (25 ml) and 1,8-diazabicyclo[5.4.0]undec-7-ene (DBU, 600 mg) and stirred at 50° C. for 1.0 h. At the end of reaction, diethylether (30 ml) was added to effect precipitation of solids which were separated by a centrifuge technique and repeatedly washed with a mixture of tetrahydrofuran and diethylether. The resulting brown solids were dried in vacuum at 40° C. to afford the corresponding mercaptosuccinic acid derivatives of fullerenes, $C_{60}[-SCH_2(CO_2H)CH_2CO_2H]_n$, (415 mg). The physical data of these compounds are as follows: $IRv_{max}$ (KBr) 3425 (s, OH), 2910 (C—H), 2608–2534 (CO$_2$H), 1700 (s) 1623, 1544, 1392, 1388, 1307, 1263, 1202, 1173, 1056, and 525 cm$^{-1}$.

EXAMPLE 22

Synthesis of Poly(hexylmercapto)fullerenes, $C_{60}[-SCH_2CH_2CH_2CH_2CH_2CH_3]_n$ A round-bottom reaction flask (100 ml) equipped with a magnetic stirrer was fitted with a septum and a cool-trap condenser. It was charged with sodium (100 mg) and tetrahydrofuran (25 ml). The mixture was added hexanethiol (420 mg) and stirred for 1 h to afford a sodium hexylthiolate solution. The solution was then added $C_{60}(NO_2)_n$ (400 mg) in tetrahydrofuran (25 ml) and stirred at ambient temperatures for an additional 2 h. At the end of reaction, all solvents in the solution were removed via vaccuo to obtain brown solid products, which were washed twice with water and acetone. The resulting brown solids were dried in vacuum at 40° C. to afford the corresponding poly(hexylmercapto) fullerenes, $C_{60}[-SCH_2CH_2CH_2CH_2CH_2CH_3]_n$, (465 mg). The physical data of these compounds are as follows: $IRv_{max}$ (KBr) 2953 (C—H), 2921 (C—H), 2848 (C—H), 1644, 1459, 1428, 1384, 1183, 1045, 793, 729, 577, and 526 cm$^{-1}$.

EXAMPLE 23

Synthesis of Poly(acetylacetonato)fullerenes, $C_{60}[-CH(COCH_3)_2]_m$

A round-bottom reaction flask (100 ml) equipped with a magnetic stirrer was fitted with a septum and a cool-trap condenser. It was charged with 2,4-pentanedione (350 mg) and tetrahydrofuran (20 ml). The mixture was added lithium diisopropylamine in tetrahydrofuran (1.1 equiv of 2,4-pentanedione) and stirred for 1 h to afford the corresponding lithium acetylacetonate. The solution was then added $C_{60}$ $(NO_2)_n$ (400 mg) in tetrahydrofuran (25 ml) and stirred at ambient temperatures for an additional 2 h. At the end of reaction, the mixture was quenched with H$_2$O to give precipitation of products, which were separated from the mother liquor by centrifuge. The solids were washed with diethylether (30 ml), twice with benzene (20 ml each time), twice with acetone (20 ml each time), and dried in vacuum at 40° C. to afford brown solids of the corresponding poly(acetyl-acetonato)fullerenes (380 mg), $C_{60}[-CH(COCH_3)_2]_m$, where m≧n. The physical data of poly (acetylacetonato)fullerenes are as follows: $IRv_{max}$ (KBr) 3401 (s, OH), 2979 (C—H), 2927 (C—H), 2881 (C—H), 1702, 1620, 1426, 1380, 1361, 1260, 1183, 1057, 953, and 532 cm$^{-1}$.

EXAMPLE 24

Synthesis of Poly[bis(1,1'-hydroxyaminoethyl) methyl]fullerenes, $C_{60}\{-CH[C(OH)(NH_2)CH_3]_2\}_m$ A round-bottom reaction flask (100 ml) equipped with a magnetic stirrer was fitted with a septum and a cool-trap condenser. It was charged with 2,4-pentanedione (350 mg) and tetrahydrofuran (20 ml). The mixture was added lithium diisopropylamine in tetrahydrofuran (1.1 equiv of 2,4-pentane-dione) and stirred for 1 h to afford the corresponding lithium acetylacetonate. The solution was then added $C_{60}(NO_2)_n$ (400 mg) in tetrahydrofuran (25 ml) and stirred at ambient temperatures for an additional 2 h. At the end of reaction, the mixture was quenched with ammonium iodide, $NH_4^+I^-$, and stirred for 1 h. Tetrahydrofuran was then removed from the solution to give semi-solid of products, which were washed repeatedly with water and acetone, and dried in vacuum at 40° C. to afford brown solids of the corresponding poly[bis(1,1'-hydroxyaminoethyl)methyl] fullerenes, $C_{60}\{-CH[C(OH)(NH_2)CH_3]_2\}_m$, where m≧n. The physical data of these compounds are as follows: $IR\nu_{max}$ (KBr) 3400 (s), 3151 (s), 3043, 2929 (C—H), 2880 (C—H), 1635, 1401, 1220, 1035, 773, 630, and 545 cm$^{-1}$.

EXAMPLE 25

Synthesis of Poly[methoxyoligo (ethyleneglycolated)]fullerenes, $C_{60}[-O(CH_2-CH_2O)_3$ or $_{12-13}CH_3]_m$ A round-bottom reaction flask (100 ml) equipped with a magnetic stirrer was fitted with a septum and a cool-trap condenser. It was charged with polyethylene glycol monomethylether, $HO(CH_2CH_2O)_3CH_3$ or $HO(CH_2CH_2O)_{12-13}CH_3$, (1.3 equiv of nitro groups in polynitro fullerene) and tetrahydrofuran (20 ml). The mixture was added sodium (1.2 equiv of —OH) and stirred for 1 h to afford the corresponding $NaO(CH_2CH_2O)_pCH_3$. The solution was then added $C_{60}(NO_2)_n$ (400 mg) in tetra-hydrofuran (25 ml) and stirred at ambient temperatures for an additional 2 h. At the end of reaction, water (0.2 ml) was added and tetrahydrofuran was evaporated from the resulting solution to afford pale brown to brown solids. The solid was added into hexane (100 ml) with stirring to give fine suspension of products. The solid precipitate was isolated by a centrifuge technique. It was then dissolved in tetrahydro-furan, filtered, and purified by chromatography ($SiO_2$) using ethylacetate as an eluent, where all unreacted polyethylene glycol monomethylether was removed ($R_f$=0.85). Solids in a brown band on the thin-layer chromatographic plate ($R_f$=0.2) were recovered and dried in vacuum at 40° C. to afford pale brown to brown solids of the corresponding poly[methoxy-oligo (ethylene glycolated)]fullerenes, $C_{60}[-O(CH_2CH_2O)_3CH_3]_m$ or $C_{60}[-O(CH_2CH_2O)_{12-13}CH_3]_m$, where m≧n. The physical data of $C_{60}[-O(CH_2CH_2O)_{12-13}CH_3]_m$ are as follows: $IR\nu_{max}$(KBr) 3435 (s), 2920 (C—H), 2874 (C—H), 2835, 1593 (s), 1453, 1410, 1367, 1270, 1105 (s), 949, 776, 623, and 455 cm$^{-1}$. $^1H$ NMR (300 MHz, DMSO-$d_6$) δ 3.22 ($CH_3$) and 3.40 ($CH_2$).

EXAMPLE 26

Synthesis of Functionalized Polyorganofullerene Derivatives, $C_{60}(-A-B-Z)_m$

A round-bottom reaction flask (100 ml) equipped with a magnetic stirrer was fitted with a septum and a cool-trap condenser. It was charged with either $HO-Y_1$, $H_2N-Y_1$, $HS-Y_1$, $HO-C_6H_4-Y_1$, $HS-CS-Y_1$, or $H_2N-CO-Y_1$ (1.3 equiv of nitro groups in polynitro fullerene) and tetrahydrofuran (20 ml). The mixture was added superhydride (1.1 equiv of —OH, —$NH_2$, or —SH groups, 1.0 M in tetrahydrofuran) and stirred for 1 h to afford the corresponding lithium salts of $LiO-Y_1$, $LiNH-Y_1$, $LiS-Y_1$, $LiO-C_6H_4-Y_1$, $LiS-CS-Y_1$, or $LiHN-CO-Y_1$. The solution was then added $C_{60}(NO_2)_n$ (400 mg) in tetrahydrofuran (25 ml) and stirred at ambient temperatures for an additional 2 h. At the end of reaction, tetra-hydrofuran was evaporated from the resulting solution to afford pale brown to brown solids. The solid was added into diethylether (100 ml) with stirring to give fine suspension of products. The solid precipitate was isolated by a centrifuge technique. It was then washed twice with diethyl ether (20 ml each time), twice with acetone (20 ml each time), and dried in vacuum at 40° C. to afford pale brown to brown solids of the corresponding functionalized polyorgano fullerene derivatives, $C_{60}(-A-B-Z)_m$, where m≧n, A, independently, is —O—, —NH—, —S—, —O—$C_6H_4$—, —HN—CO—; B, independently, is —R—O—[$Si(CH_3)_2$—O—]$_{1-100}$, $C_{1-200}$ alkyl, $C_{6-50}$ aryl, $C_{7-100}$ alkylaryl, $C_{7-100}$ arylalkyl, ($C_{2-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{2-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$; each Z, independently, is —C—D—, wherein each C, independently, is —R—, —R—Ar—, —Ar—R—, or —Ar—; and each D, independently, is —H, —O—$Si(CH_3)_3$, —S—$CH_2$—Ar, —$SO_3^-$, —$CO_2^-$, —O—$PO_3^{-2}$, —O—PO(O)—O—$PO_3^{-2}$, or —$NR_1R_2$, wherein each of R, $R_1$, $R_2$, $R_3$ is independently $C_{1-20}$ alkyl and each Ar, independently, is aryl.

EXAMPLE 27

Synthesis of Polyhydroxymercaptosuccinic Acid Derivatives of Fullerenes (FSSA—OH), $C_{60}[-SCH_2(CO_2H)CH_2CO_2H]_n(OH)_m$ A round-bottom reaction flask (100 ml) equipped with a magnetic stirrer was fitted with a septum and a cool-trap condenser. It was charged with mercaptosuccinic acid derivatives of fullerenes (FSSA, 200 mg), $C_{60}[-SCH_2(CO_2H)CH_2CO_2H]_n$ prepared by a method shown in Example 13, sodium hydroxide (2.5 g), tetrabutylammonium hydroxide (1.0 ml, 2.0 M in $H_2O$), and $H_2O$ (20 ml). The mixture was stirred at 40° C. for 4 h. At the end of reaction, the resulting solution was added methanol (200 ml) to effect precipitation of brown solids. The precipitated solid was isolated by a centrifuge technique. It was then washed twice with methanol (20 ml each) and dried in vacuum at 40° C. to afford the corresponding sodium salts of polyhydroxymercaptosuccinic acid derivatives of fullerene (215 mg), $C_{60}[-SCH_2(CO_2Na)CH_2CO_2Na]_n-(OH)_m$. The treatment of these sodium salts with an aqueous solution of HCl (1.0 N) at ambient temperature for 0.5 h gave $C_{60}[-SCH_2(CO_2H)CH_2CO_2H]_n(OH)_m$ (FSSA—OH) in a quantitative yield. The physical data of $C_{60}[-SCH_2(CO_2Na)CH_2CO_2Na]_n-(OH)_m$ are as follows: $IR\nu_{max}$ (KBr) 3450 (broad, s), 2925 (w, C—H), 2870 (w, C—H), 1623 (s), 1589 (s), 1392, 1055, and 690 (broad) cm$^{-1}$. $^1H$ NMR (200 MHz, $D_2O$) δ 3.59 (t, CH), 2.82 (broad, OH), and 2.62 (d, $CH_2$).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the following formula:

wherein

F is a fullerene core;

each E, independently, is $E_1$, $E_2$, $E_3$, $E_4$, or $E_5$; wherein each $E_1$, independently, is $Y_1,Y_2$-amino, $(Y_1,Y_2$-alkyl)amino, $Y_1,Y_2$-ethylenediamino, (dihydroxymethyl)alkylamino, $(X_1,X_3$-aryl)amino, or $X_1,X_3$-aryloxy; each $E_2$, independently, is $Y_1,Y_2$-alkoxy, $(Y_1,Y_2$-amino)alkoxy, $(Y_1,Y_2,Y_3$-aryl)oxy, (dihydroxyalkyl)aryloxy, $(Y_1,Y_2,Y_3$-alkyl)amino, $(Y_1,Y_2,Y_3$-aryl)amino, or dihydroxyalkylamino; each $E_3$, independently, is $Y_1,Y_2,Y_3$-alkoxy, (trihydroxyalkyl)alkoxy, (trihydroxyalkyl)alkylamino, (dicarboxyalkyl)amino, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl; each $E_4$, independently, is ((glycosidyl)oxoheteroaryl)amino, ((glycosidyl)oxoaryl)amino, $(X_1,X_2,X_3$-heteroaryl)amino, $(X_1$-diarylketone)amino, $(X,X_1$-oxoaryl)amino, $(X,X_1$-dioxoaryl)amino, $(Y_1$-alkyl,$Y_2$-alkyldioxoheteroaryl)amino, $(Y_1$-alkyl,$Y_2$-alkyldioxoaryl)amino, $(di(Y_1,Y_2$-methyl)dioxoheteroaryl)amino, $(di(Y_1,Y_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl)amino, ((isopropylaminohydroxy-alkoxy)aryl)amino, or $(X_1,X_2,X_3$-alkylaryl)amino; each $E_5$, independently, is $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(X,X_1$-oxoaryl)oxy, $(X_1,X_2$-dioxoaryl)oxy, $(Y_1,Y_2$,diaminodihydroxy)alkyl, $(X_1,X_2$-heteroaryl)thio, ((tricarboxylalkyl)ethylenediamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$,-alkyl(thiocarbonyl)thio, $Y_1,Y_2,Y_3$-alkyl(thiocarbonyl)thio, $(Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-20}$amino, or (pyranosyl) amino;

each X, independently, is halide; each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$;

each of $Y_1$, $Y_2$, and $Y_3$ independently, is —B—Z; each B, independently, is —$R_a$—O—[Si(CH$_3$)$_2$—O—]$_{1-100}$, $C_{1-2000}$ alkyl, $C_{6-40}$ aryl, $C_{7-60}$ alkylaryl, $C_{7-60}$ arylalkyl, ($C_{1-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{14-60}$ aryl urethane)$_{1-100}$, ($C_{10-80}$ alkylaryl urethane)$_{1-100}$, ($C_{10-80}$ arylalkyl urethane)$_{1-100}$, ($C_{5-50}$ alkyl urea)$_{1-100}$, ($C_{14-60}$ aryl urea)$_{1-100}$, ($C_{10-80}$ alkylaryl urea)$_{1-100}$, ($C_{10-80}$ arylalkyl urea)$_{1-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{1-100}$, ($C_{7-50}$ aryl carbonate)$_{1-100}$, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$;

each Z, independently, is —C—D—, wherein each C, independently, is —R—, —R—Ar—, —Ar—R—, or —Ar—; and each D, independently, is —OH, —SH, —NH$_2$, —NHOH, —SO$_3$H, —OSO$_3$H, —COOH, —CONH$_2$, —CO—NH—NH$_2$, —CH(NH$_2$)—COOH, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, -glycoside, —OCH$_3$, —O—CH$_2$—(CHOH)$_4$—CH$_2$OH, —O—CH$_2$—(CHOH)$_2$—CH$_2$OH, —C$_6$H$_3$(OH)$_2$, —NH$^{3+}$, —N$^+$H$_2$R$_b$, —N$^+$HR$_b$R$_c$, or N$^+$HR$_b$R$_c$R$_d$; wherein each of R, $R_1$, $R_2$, $R_3$, $R_a$, $R_b$, $R_c$ and $R_d$, independently, is $C_{1-30}$ alkyl, each Ar, independently, is aryl, and n is 2–30;

and a salt thereof.

2. The compound of claim 1, wherein F is a fullerene core of $C_{60}$, $C_{70}$, $C_{76}$, $C_{78}$, $C_{82}$, $C_{84}$, or $C_{92}$.

3. The compound of claim 1, wherein each E, independently, is $E_2$, $E_3$, $E_4$, or $E_5$.

4. The compound of claim 1, wherein n=3 to 25.

5. The compound of claim 4, wherein each E, independently, is $E_3$, $E_4$, or $E_5$.

6. The compound of claim 5, wherein each $X_1$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$.

7. The compound of claim 6, wherein each B, independently, is —$R_a$—O—[Si(CH$_3$)$_2$—O—]$_{1-100}$, $C_{6-40}$ aryl, $C_{7-60}$ alkylaryl, $C_{7-60}$ arylalkyl, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{14-60}$ aryl urethane)$_{1-100}$, ($C_{10-80}$ alkylaryl urethane)$_{1-100}$, ($C_{10-80}$ arylalkyl urethane)$_{1-100}$, ($C_{5-50}$ alkyl urea)$_{1-100}$, ($C_{14-60}$ aryl urea)$_{1-100}$, ($C_{10-80}$ alkylaryl urea)$_{1-100}$, ($C_{10-80}$ arylalkyl urea)$_{1-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{1-100}$, ($C_{7-50}$ aryl carbonate)$_{1-100}$, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$;

wherein each of R, $R_a$, $R_1$, $R_2$, and $R_3$, independently, is $C_{1-30}$ alkyl, and each Ar, independently, is aryl.

8. The compound of claim 6, wherein each D, independently, is —SH, —NHOH, —$SO_3H$, —$OSO_3H$, —$CONH_2$, —CO—NH—$NH_2$, —CH($NH_2$)—COOH, —P(OH)$_3$, —PO(OH)$_2$, —O—PO(OH)$_2$, —O—PO(OH)—O—PO(OH)$_2$, —O—PO(O)—O—$CH_2CH_2NH_3^+$, -glycoside, —O—$CH_2$—(CHOH)$_4$—$CH_2OH$, —O—$CH_2$—(CHOH)$_2$—CHOH, —$C_6H_3$(OH)$_2$, —$N^+HR_bR_c$, or $N^+HR_bR_cR_d$, wherein each of R, $R_b$, $R_c$, $R_d$, independently, is $C_{1-30}$ alkyl and each Ar, independently, is aryl.

9. The compound of claim 1, wherein n is 4–20.

10. The compound of claim 9, wherein each E, independently, is $E_4$ or $E_5$.

11. The compound of claim 10, wherein each $X_1$, independently, is —$Y_1$, —O—$Y_1$, —S—$Y_1$, —NH—$Y_1$, —CO—O—$Y_1$, —O—CO—$Y_1$, —CO—NH—$Y_1$, —CO—$NY_1Y_2$, —NH—CO—$Y_1$, —$SO_2$—$Y_1$, —$CHY_1Y_2$, or —$NY_1Y_2$.

12. The compound of claim 11, wherein each B, independently, is —$R_a$—O—[Si($CH_3$)$_2$—O—]$_{1-100}$, $C_{6-40}$ aryl, $C_{7-60}$ alkylaryl, $C_{7-60}$ arylalkyl, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{14-60}$ aryl urethane)$_{1-100}$, ($C_{10-80}$ alkylaryl urethane)$_{1-100}$, ($C_{10-80}$ arylalkyl urethane)$_{1-100}$, ($C_{5-50}$ alkyl urea)$_{1-100}$, ($C_{14-60}$ aryl urea)$_{1-100}$, ($C_{10-80}$ alkylaryl urea)$_{1-100}$, ($C_{10-80}$ arylalkyl urea)$_{1-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{1-100}$, ($C_{7-50}$ aryl carbonate)$_{1-100}$, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$;

wherein each of R, $R_a$, $R_1$, $R_2$, and $R_3$, independently, is $C_{1-30}$ alkyl, and each Ar, independently, is aryl.

13. The compound of claim 11, wherein each D, independently, is —SH, —NHOH, —$SO_3H$, —$OSO_3H$, —$CONH_2$, —CO—NH—$NH_2$, —CH($NH_2$)—COOH, —P(OH)$_3$, —PO(OH)$_2$, —O—PO(OH)$_2$, —O—PO(OH)—O—PO(OH)$_2$, —O—PO(O)—O—$CH_2CH_2NH_3^+$, -glycoside, —O—$CH_2$—(CHOH)$_4$—$CH_2OH$, —O—$CH_2$—(CHOH)$_2$—CHOH, —$C_6H_3$(OH)$_2$, —$N^+HR_bR_c$, or $N^+HR_bR_cR_d$, wherein each of R, $R_b$, $R_c$, $R_d$, independently, is $C_{1-30}$ alkyl and Ar is independently aryl.

14. A method of preparing a polyorganofullerene derivative of the following formula:

F(—E)$_n$ 

wherein

F is a fullerene core;

each of each E, independently, is $E_1$, $E_2$, $E_3$, $E_4$, $E_5$ or $E_6$; in which each $E_1$, independently, is $Y_1,Y_2$-amino, $(Y_1,Y_2$-alkyl)-amino, $Y_1,Y_2$-ethylenediamino, (dihydroxymethyl) alkylamino, $(X_1,X_3$-aryl)amino, or $X_1,X_3$-aryloxy; each $E_2$, independently, is $Y_1,Y_2$-alkoxy, $(Y_1,Y_2$-amino)alkoxy, $(Y_1,Y_2,Y_3$-aryl)oxy, (dihydroxyalkyl) aryloxy, $(Y_1,Y_2,Y_3$-alkyl)amino, $(Y_1Y_2,Y_3$-aryl) amino, or dihydroxyalkylamino; each $E_3$, independently, is $Y_1,Y_2,Y_3$-alkoxy, (trihydroxyalkyl) alkoxy, (trihydroxyalkyl)alkylamino, (dicarboxyalkyl) amino, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl; each $E_4$, independently, is ((glycosidyl)oxoheteroaryl) amino, ((glycosidyl)oxoaryl)amino, $(X_1,X_2,X_3$-heteroaryl)amino, $(X_1$-diarylketone)amino, $(X,X_1$-oxoaryl)amino, $(X,X_1$-dioxoaryl)amino, $(Y_1$-alkyl,$Y_2$-alkyldioxoheteroaryl)amino, $(Y_1$-alkyl,$Y_2$-alkyldioxoaryl)amino, $(di(Y_1,Y_2$-methyl) dioxoheteroaryl)amino, $(di(Y_1,Y_2$-methyl)dioxoaryl) amino, ((glycosidyl)heteroaryl)amino, ((glycosidyl) aryl)amino, ((carboxylacetylalkyl)oxoheteroaryl) amino, ((carboxylacetylalkyl)oxoaryl)amino, ((isopropylaminohydroxy-alkoxy)aryl)amino, or $(X_1, X_2,X_3$-alkylaryl)amino; each $E_5$, independently, is $(X_1, X_2,X_3$-heteroaryl)oxy, (isopropylaminohydroxyalkyl) aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(X,X_1$-oxoaryl)oxy, $(X_1,X_2$-dioxoaryl)oxy, $(Y_1,Y_2,$diaminodihydroxy)alkyl, $(X_1, X_2$-heteroaryl)thio, ((tricarboxylalkyl) ethylenediamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$,-alkyl(thiocarbonyl)thio, $Y_1,Y_2,Y_3$-alkyl (thiocarbonyl)thio, $(Y_1,Y_2$-aminothiocarbonyl)thio, (pyranosyl)thio, cysteinyl, tyrosinyl, (phenylalainyl) amino, (dicarboxyalkyl)thio, $(aminoaryl)_{1-20}$amino, or (pyranosyl) amino; each $E_6$, independently, is $Y_1$-amino, $Y_1$-alkoxy, or $Y_1$-thio;

each X, independently, is halide; each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$;

each of $Y_1$, $Y_2$, and $Y_3$ independently, is —B—Z;

each B, independently, is —R$_a$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$, (C$_{6-40}$ aryl ether)$_{1-100}$, (C$_{7-60}$ alkylaryl ether)$_{1-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$;

each Z, independently, is —C—D—, wherein each C, independently, is independently —R—, —R—Ar—, —Ar—R—, or —Ar—; and each D, independently, is —H, —OH, —SH, —NH$_2$, —NHOH, —SO$_3$H, —OSO$_3$H, —COOH, —CONH$_2$, —CO—NH—NH$_2$, —CH(NH$_2$)—COOH, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, -glycoside, —OCH$_3$, —O—CH$_2$—(CHOH)$_4$—CH$_2$OH, —O—CH$_2$—(CHOH)$_2$—CH$_2$OH, —C$_6$H$_3$(OH)$_2$, —NH$^{3+}$, —N$^+$H$_2$R$_b$, —N$^+$HR$_b$R$_c$, or N$^+$HR$_b$R$_c$R$_d$; wherein each of R, R$_1$, R$_2$, R$_3$, R$_a$, R$_b$, R$_c$ and R$_d$, independently, is C$_{1-30}$ alkyl and each Ar, independently, is aryl; and n is 1–30; said method comprising:

contacting a polynitrofullerene or polycyclosulfated fullerene intermediate with a nucleophilic agent to produce a corresponding polyorganofullerene derivative covered by the formula recited above.

15. The method of claim 14, wherein the intermediate is a polynitrofullerene.

16. The method of claim 14, wherein the intermediate is a polycyclosulfated fullerene.

17. The method of claim 15, further comprising hydrolyzing the polyorganofullerene derivative thus obtained to afford a corresponding polyhydroxyorganofullerene derivative of the following formula:

$$F(-E)_n(OH)_m$$

wherein m is 1–20.

18. The method of claim 16, further comprising hydrolyzing the polyorganofullerene derivative thus obtained to afford a corresponding polyhydroxyorganofullerene derivative of the following formula:

$$F(\!-\!E)_n(OH)_m$$

wherein m is 1–20.

* * * * *